United States Patent
Brown et al.

(10) Patent No.: US 7,238,520 B2
(45) Date of Patent: Jul. 3, 2007

(54) PCR SAMPLE PREPARATION HOLDER AND METHOD

(75) Inventors: Drew Chapman Brown, Towson, MD (US); Carrie Lynn Holmes, Bel Air, MD (US); Eric Scott Clasen, Hillsborough, NJ (US); Richard Karl Pallo, New Hope, PA (US); Michael Joseph Rello, Harleysville, PA (US); Lisa Miller, Cockeysville, MD (US); Tiffany Howland, Pasadena, MD (US)

(73) Assignee: Smiths Detection Inc., Edgewood, MD (US)

( * ) Notice: Subject to any disclaimer, the term of this patent is extended or adjusted under 35 U.S.C. 154(b) by 322 days.

(21) Appl. No.: 10/727,037

(22) Filed: Dec. 4, 2003

(65) Prior Publication Data

US 2004/0214200 A1 Oct. 28, 2004

Related U.S. Application Data

(60) Provisional application No. 60/430,994, filed on Dec. 4, 2002.

(51) Int. Cl.
*C12M 1/34* (2006.01)
*C12M 3/00* (2006.01)
*B01L 3/02* (2006.01)
*B32B 5/02* (2006.01)
*B32B 27/04* (2006.01)

(52) U.S. Cl. ............... 435/287.6; 435/288.2; 435/287.2; 435/91.2; 435/288.1; 422/58; 422/99; 422/100; 600/575

(58) Field of Classification Search ............. 435/288.2, 435/287.6
See application file for complete search history.

(56) References Cited

U.S. PATENT DOCUMENTS

| | | | |
|---|---|---|---|
| 4,562,043 A * | 12/1985 | Mennen et al. ............... 422/56 |
| 5,084,045 A * | 1/1992 | Helenowski ................. 606/32 |
| 5,543,115 A | 8/1996 | Karakawa |
| 5,935,864 A * | 8/1999 | Schramm et al. ........... 436/174 |
| 6,180,395 B1 | 1/2001 | Skiffington et al. |
| 6,328,931 B1 * | 12/2001 | Silver et al. .................. 422/52 |
| 6,634,243 B1 * | 10/2003 | Wickstead et al. ....... 73/863.23 |
| 2002/0001539 A1 | 1/2002 | Dicesare et al. |
| 2003/0113906 A1 * | 6/2003 | Sangha et al. ........... 435/287.2 |
| 2004/0184966 A1 * | 9/2004 | Zhou et al. ................. 422/102 |

FOREIGN PATENT DOCUMENTS

EP 1024354 A1 8/2000

* cited by examiner

*Primary Examiner*—Gladys J P Corcoran
*Assistant Examiner*—Nathan A. Bowers
(74) *Attorney, Agent, or Firm*—Foley and Lardner, LLP (57) ABSTRACT

A simplified Polymerase Chain Reaction (PCR) sample preparation apparatus and method of using a PCR sample preparation for both liquid and dry samples. A portable apparatus comprising a handle removably attached to a wand assembly. The handle includes a cover and a swab with an absorbent material. The wand assembly includes a buffer container for a buffer that is ruptured by a spike when the holder is inserted into the wand assembly. The apparatus may include a waste container removably attached to a tube comprising a plunger, a safety clip to prevent the plunger from depressing, and a port for introduction of a liquid sample. A filter on the waste container collects a specimen of the liquid sample for preparation as described above.

29 Claims, 10 Drawing Sheets

PCR SAMPLE PREPARATION HOLDER AND METHOD

CROSS-REFERENCE TO RELATED APPLICATIONS

This application claims priority to and the benefit of U.S. Provisional Patent Application No. 60/430,994 filed on Dec. 4, 2002, incorporated by reference herein in its entirety.

BACKGROUND

The present invention relates to a simplified Polymerase Chain Reaction (PCR) sample preparation consumable comprising a handle removably attachable to a wand assembly for dry or processed samples. The present invention also relates to a method of biological sampling for dry, liquid or processed samples.

The present invention pertains to preparing samples for Polymerase Chain Reaction (PCR) analysis in the field.

Conventional PCR analysis is a complex procedure, requiring a series of steps with laboratory equipment. Conventional PCR analysis requires skill exceeding that of most field personnel.

Conventional PCR analysis typically requires samples to be processed or treated prior to PCR analysis. A drawback to the sample processing is that it involves at least three complex steps. First, inhibitors such as humic acids and metals in the environment are removed. Second, the sample is filtered and concentrated. Third, a combination of reagents required by the PCR assay must be added to the sample.

Another drawback of conventional PCR analysis is the apparatus is not portable. Typically such conventional analysis is done at a lab, not in the field.

SUMMARY OF THE INVENTION

An object of the present invention is to provide an apparatus and method to process a sample for PCR analysis. According to an embodiment of the present invention, the apparatus is simplified so that a non-technical person with a minimum of training can perform PCR sample preparation in the field.

According to another embodiment of the present invention, an apparatus for preparing samples for PCR analysis includes a handle and a wand assembly. The handle is comprised of a swab attached to an end of the handle, and the swab includes a stabilized reagent bead located in a chamber and a sample tube that extends from an end of the chamber. The wand assembly includes a buffer container at an end of a shaft. A stand is located at another end of the shaft of the wand assembly. The handle is configured to attach to the wand assembly.

According to another embodiment of the present invention, an apparatus for preparing liquid samples includes a waste container and a tube. The tube includes a port for introduction of a liquid sample, and a plunger for pushing the liquid sample into the waste container. The tube is removably attached to the waste container.

According to another aspect of the present invention, a biological sampling method for dry and/or processed samples includes the steps of providing a handle containing an absorbent material and stabilized reagent. The method further includes wiping the absorbent material over a test surface, providing a wand assembly and inserting the handle into the wand assembly, thus rupturing a buffer container. Rupturing the buffer container releases a buffer through the absorbent material and into a chamber for mixing with the reagents and filling a sample tube.

According to another aspect of the present invention, a biological sampling method for liquid samples includes the steps of providing a waste container having a plunger and a port and introducing the liquid sample into the port. The biological sampling method further includes removing a safety clip and depressing the plunger up to a stop on the plunger, to concentrate particles in the liquid sample onto a filter. A spike ruptures a liquid container and the plunger pumps a buffer through the filter and into the waste container, washing inhibitors off the particles, such that a sample collects on the filter. The biological sampling method further includes removing the plunger and discarding the plunger, providing a swab and inserting the swab to pick up the sample from the filter in the waste container.

The apparatus for preparing samples for PCR analysis may, according to an embodiment of the present invention, be easily portable for use in the field.

The apparatus for preparing samples for PCR analysis may, according to another embodiment of the present invention, prepare liquid or dry samples.

It is to be understood that both the foregoing general description and the following detailed description are exemplary and exemplary only and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

DESCRIPTION

Hereinafter, embodiments of the present invention will be described with reference to the attached drawings.

Figure 1:
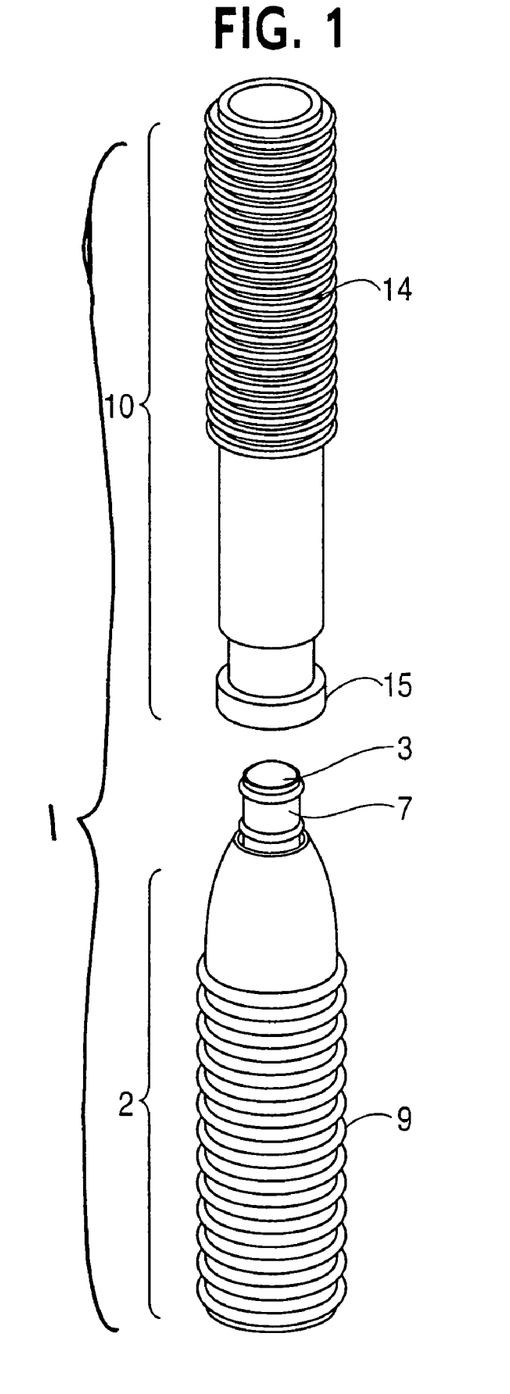
FIG. 1 is a perspective view of an embodiment of an apparatus for preparing samples for Polymerase Chain Reaction analysis according to the present invention.

An apparatus 1 for preparing a sample for PCR analysis is disclosed in FIG. 1. The apparatus 1 includes a handle 2 removably attached to a wand assembly 10. The handle 2 includes a cover 9 attached to a swab 7. The swab 7 includes an absorbent material 3 at an end of the swab 7 further from the cover 9. The wand assembly 10 includes an extendable grip 14, a shaft 16 and a stand 15 at an end of the wand assembly 10.

A stabilized reagent 4, as can be seen in FIGS. 2, and 4–6, is located in a chamber 5. The chamber 5 is located in the swab 7 of the handle 2. The swab 7 further includes a sample tube 6 extending from an end of the chamber 5. The sample tube 6 collects a sample of a prepared substance for further analyzing.

Figure 2:
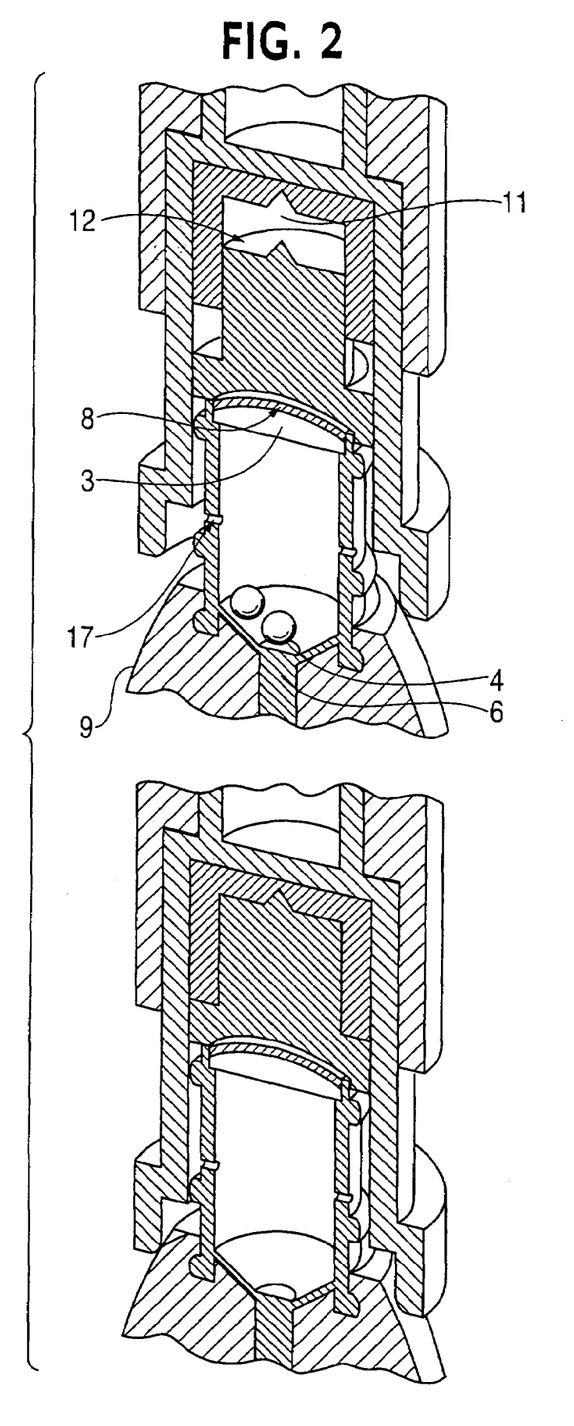
FIG. 2 is a cross-sectional view of an apparatus of FIG. 1.
Figure 3:
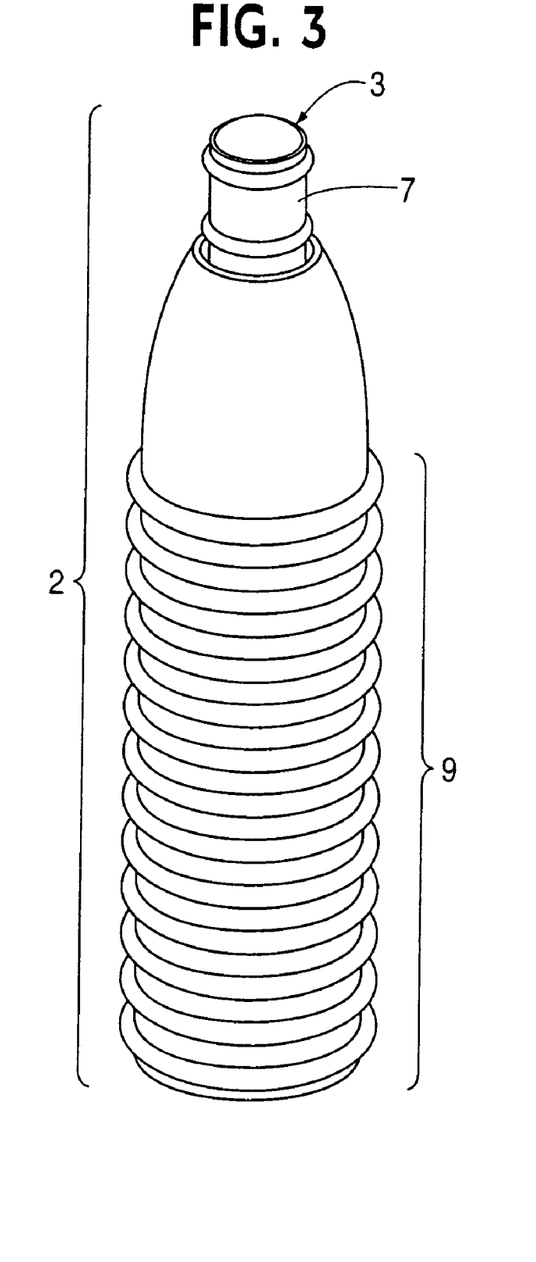
FIG. 3 is a view of the handle of the apparatus of FIG. 1.
Figure 4:
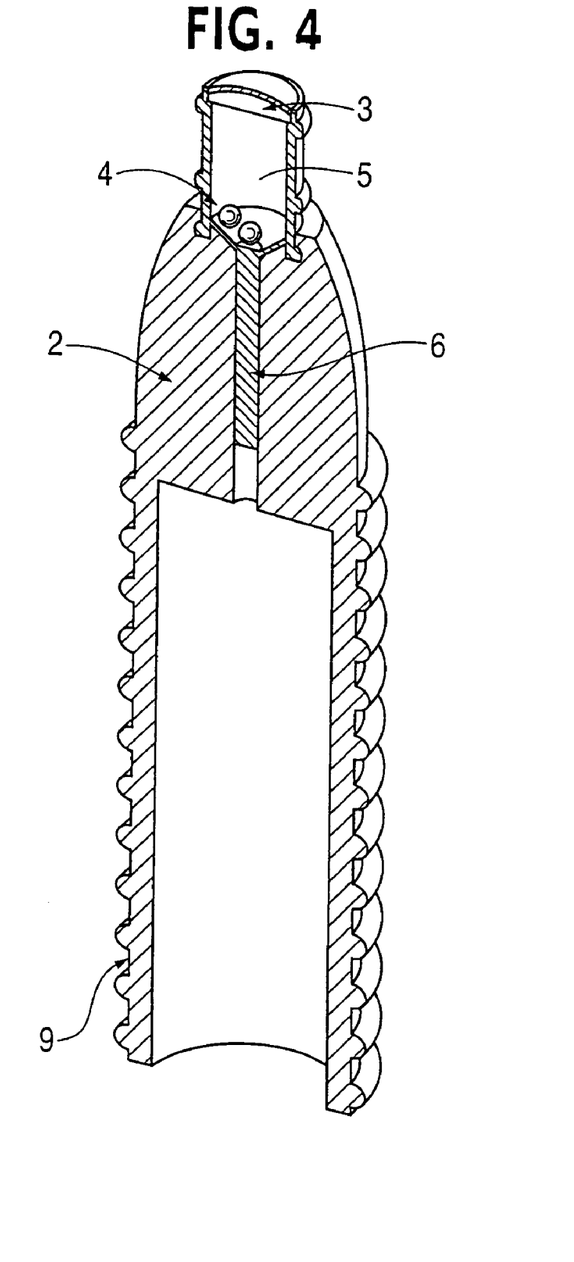
FIG. 4 is a cross-sectional view of the handle of the apparatus of FIG. 1.
Figure 5:
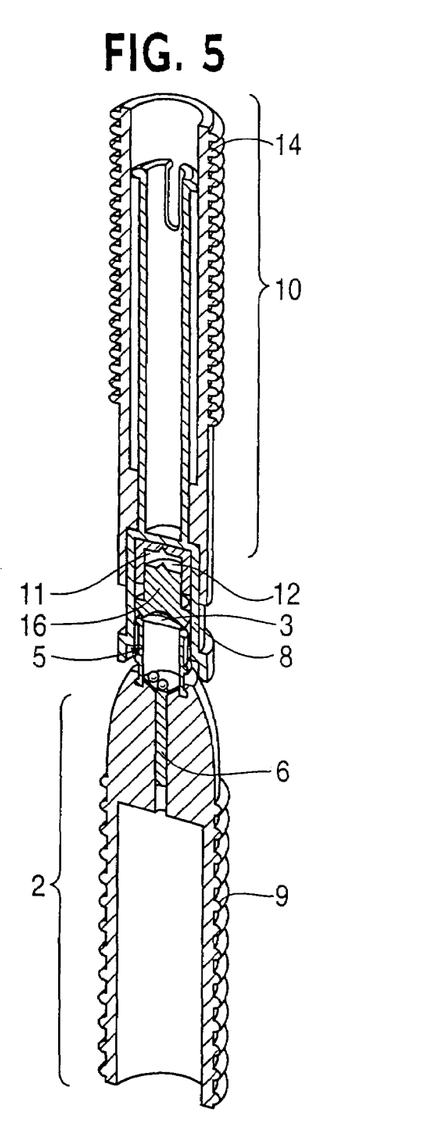
FIG. 5 is a cross-sectional view of the apparatus of FIG. 1.
Figure 6:
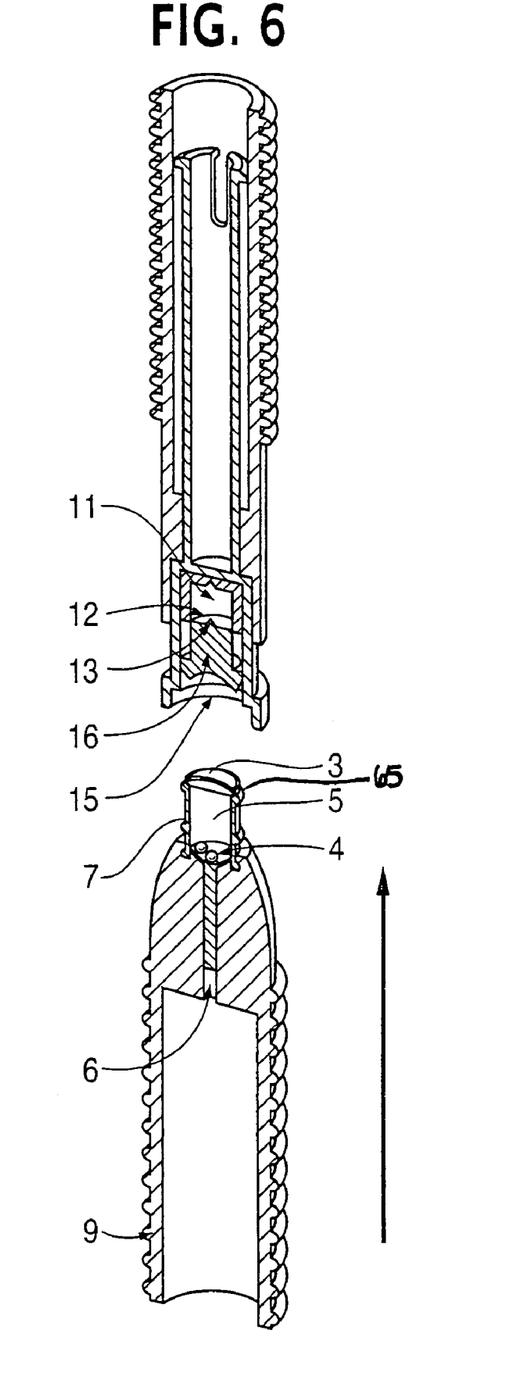
FIG. 6 is a view of the apparatus of FIG. 1.
Figure 7:
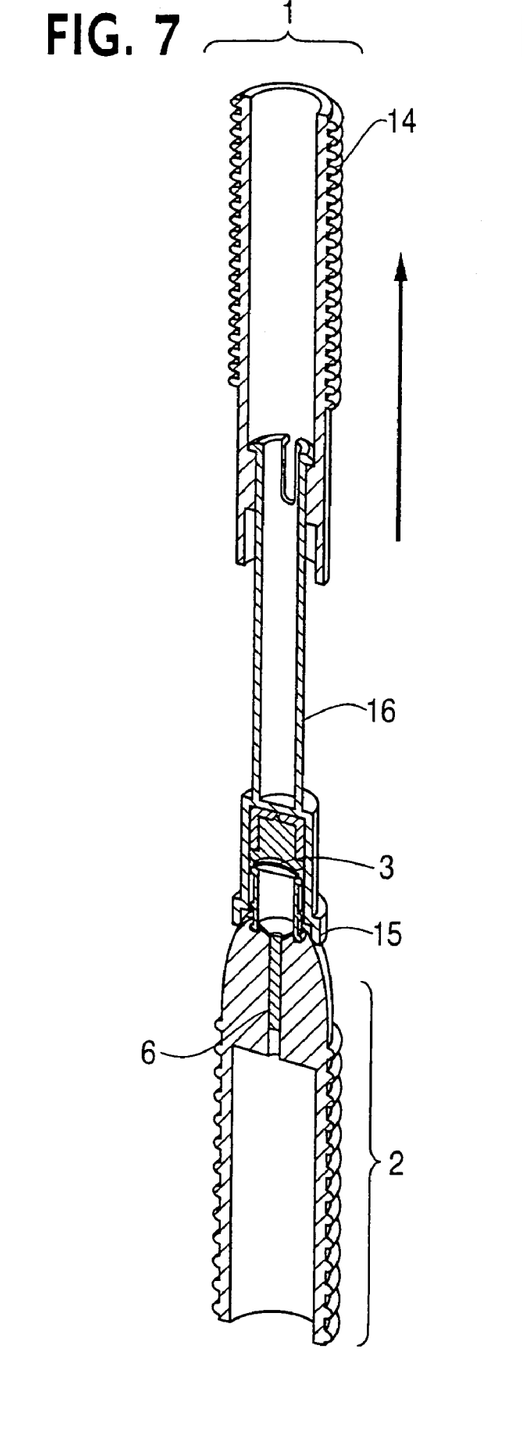
FIG. 7 is a cross-sectional view of the apparatus of FIG. 1.
Figure 8:
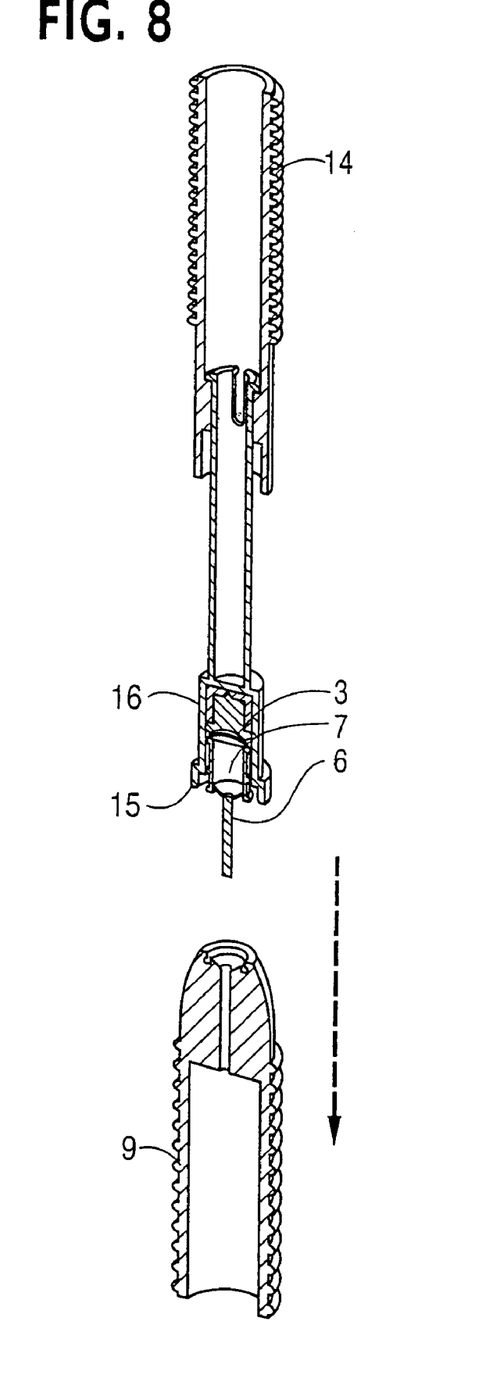
FIG. 8 is a cross-sectional view of the apparatus of FIG. 1.
Figure 9:
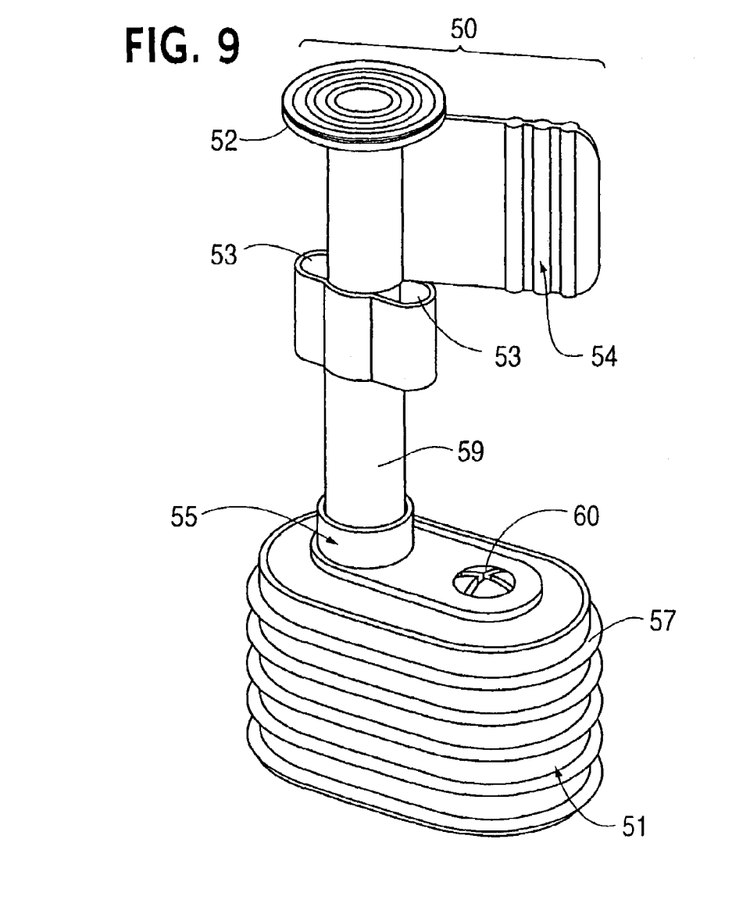
FIG. 9 is a perspective view of another embodiment of the apparatus according to the present invention.
Figure 10:
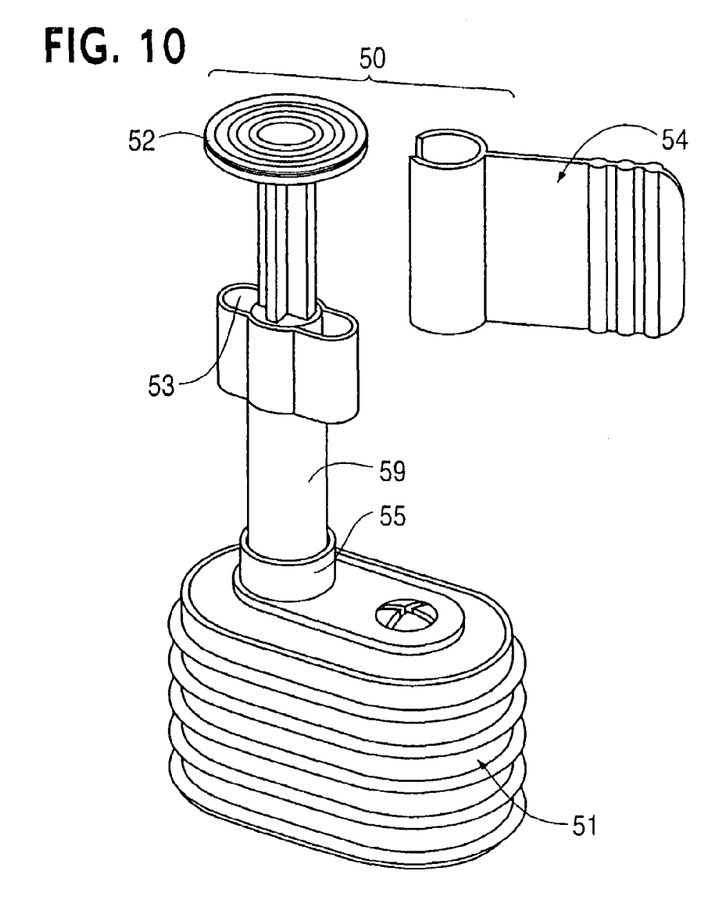
FIG. 10 is a view of the apparatus of FIG. 9.

As can be seen in FIGS. 2, 5 and 6, the wand assembly 10 further includes a buffer container 11. The buffer container 11 is positioned at an end of the shaft 16. The buffer container 11 may contain a buffer for use in analyzing a sample of a substance. The buffer container 11 includes a film 12. The film 12 covers an end of the buffer container 11.

As shown in FIG. 6, a spike 13 is positioned in the wand assembly 10. The spike 13 is configured to rupture the buffer container 11 to allow a buffer to exit the buffer container 11 and flow through the absorbent material 3 and into the chamber 5 and/or the sample tube 6. The spike 13 ruptures the film 12 of the buffer container 11 when the handle 2 is attached to the wand assembly 10.

The absorbent material 3 of the handle 2 may be IsoCode paper. The absorbent material 3 may be held onto the swab 7 by a retaining ring 65. The absorbent material 3 may be wiped over a test surface to collect a sample of a substance that is to be prepared for analysis. The absorbent material 3 may further be covered by a mesh 8, or the mesh 8 may be under the absorbent material 3.

The handle 2 and wand assembly 10 are removably attachable. The handle 2 attaches to the wand assembly 10 by inserting the swab 7 into the shaft 16 of the wand assembly 10, as shown in FIGS. 2, 5, 7, and 9. The cover 9 of the handle 2 may be configured to detach from the swab 7 after the swab 7 is fully inserted into the shaft 16 of the wand assembly 10. When the cover 9 is removed, the swab 7, with the absorbent material 3, chamber 5 and sample tube 6 remain attached to the wand assembly 10.

As can be seen in FIG. 2, the chamber 5 may include chamber vents 17. The chamber vents 17 may be sealed when the swab 7 is fully inserted into the shaft 16 of the wand assembly 10.

Figures 15A, 15B, 15C, 15D, 15E:
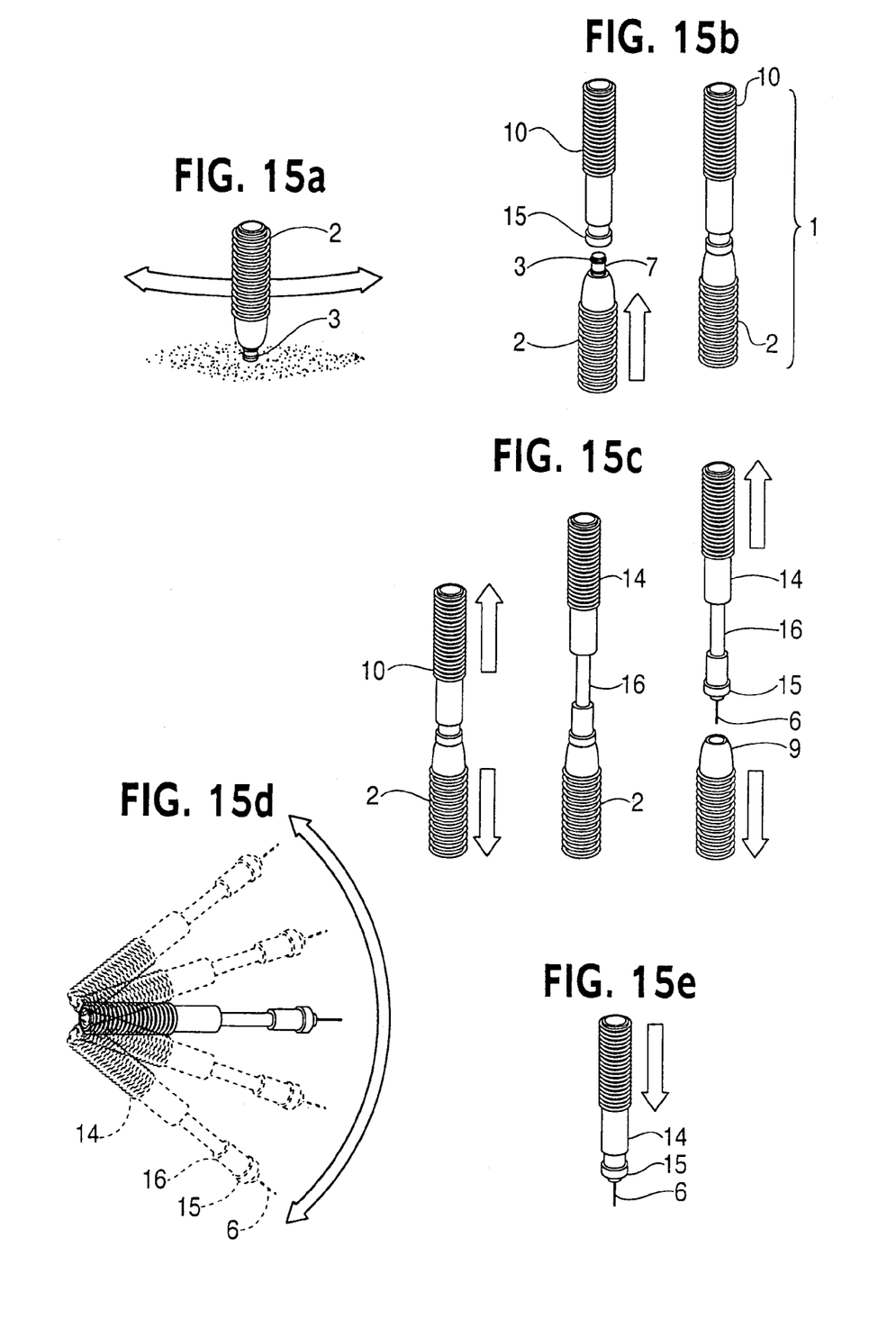
FIGS. 15a to 15e are a view of the method of using an embodiment of the apparatus according to the present invention.
Figure 16A:
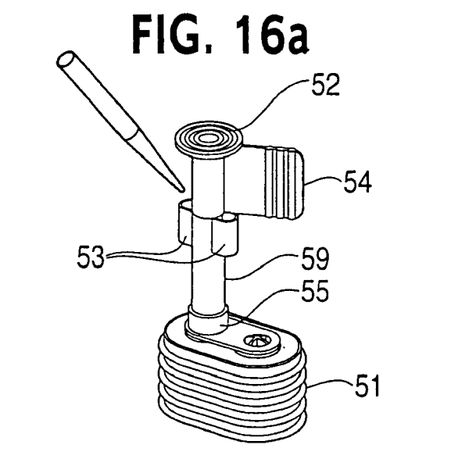
FIGS. 16a to 16f are a view of a method of using another embodiment of the apparatus according to the present invention.
Figure 16B:
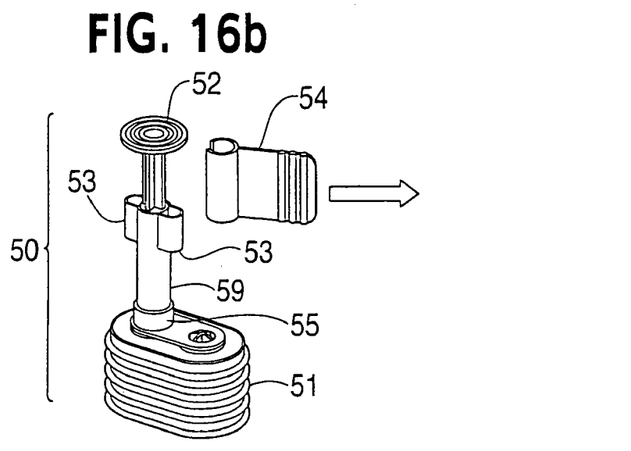
Figure 16C:
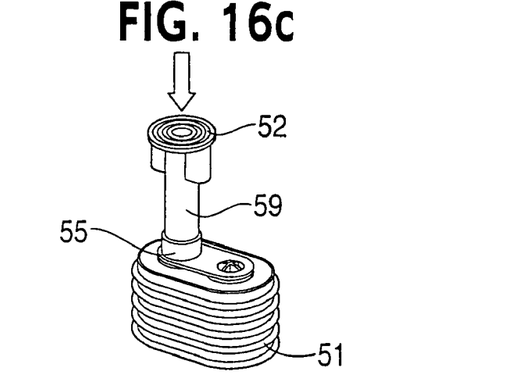
Figure 16D:
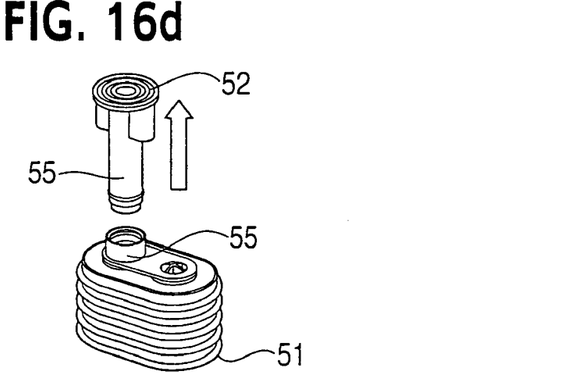
Figure 16E:
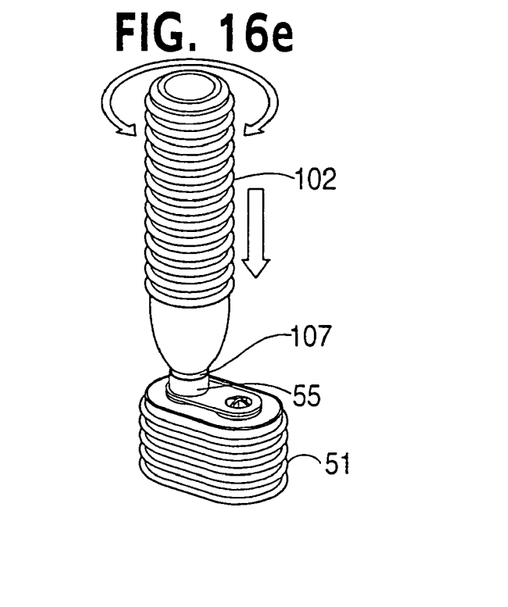
Figure 16F:
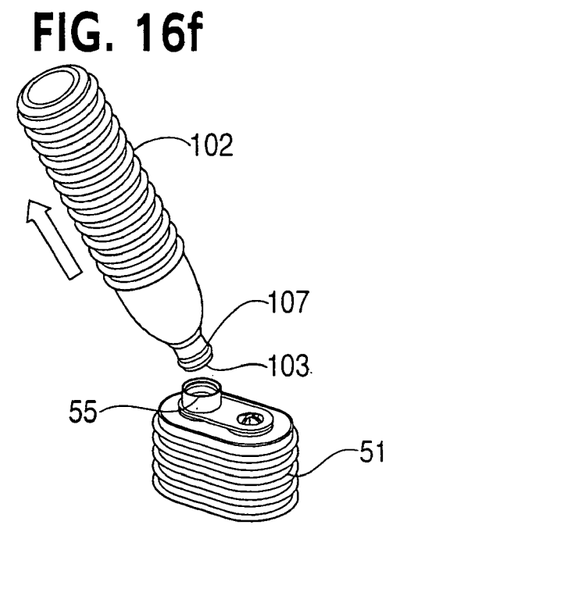

As can be seen in FIG. 15c, the grip 14 of the wand assembly 10 is extendable. A user may extend the grip 14 of the wand assembly 10 after the cover 9 is detached from the swab 7 and used to whip the apparatus 1 up and down. The whipping action enables a buffer to mix with a sample and stabilized reagent 4. The whipping action allows the mixed sample to flow through the chamber 5 and into the sample tube 6. The grip 14 may be retracted after whipping.

The stand 15 is configured to attach to or engage with a slot in a hand-held detector. When the apparatus 1 is attached to a hand-held detector by the stand 15, the sample tube 6 is inserted into a slot for further analysis of the prepared sample.

The apparatus 1 may be constructed of a suitable size and weight so that it may be easily transported for use in the field. For example, the apparatus 1 may be carried in the operator's hand for simple portability.

FIGS. 9–14 show an alternative embodiment in which, an apparatus 50 further includes a waste container 51 removably attached to a tube 59. The tube 59 includes a port 53 for the introduction of a liquid sample and a plunger 52 inserted into the tube 59 for pushing the liquid sample into the waste container 51.

A safety clip 54 may be removably attached to the plunger 52. The safety clip 54 is configured to clip onto the plunger 52 to prevent the plunger 52 from depressing prior to introduction of a liquid sample into the port 53. The safety clip 54 may be removed after a liquid sample is introduced into the port 53 to be prepared for analysis.

Figure 12:
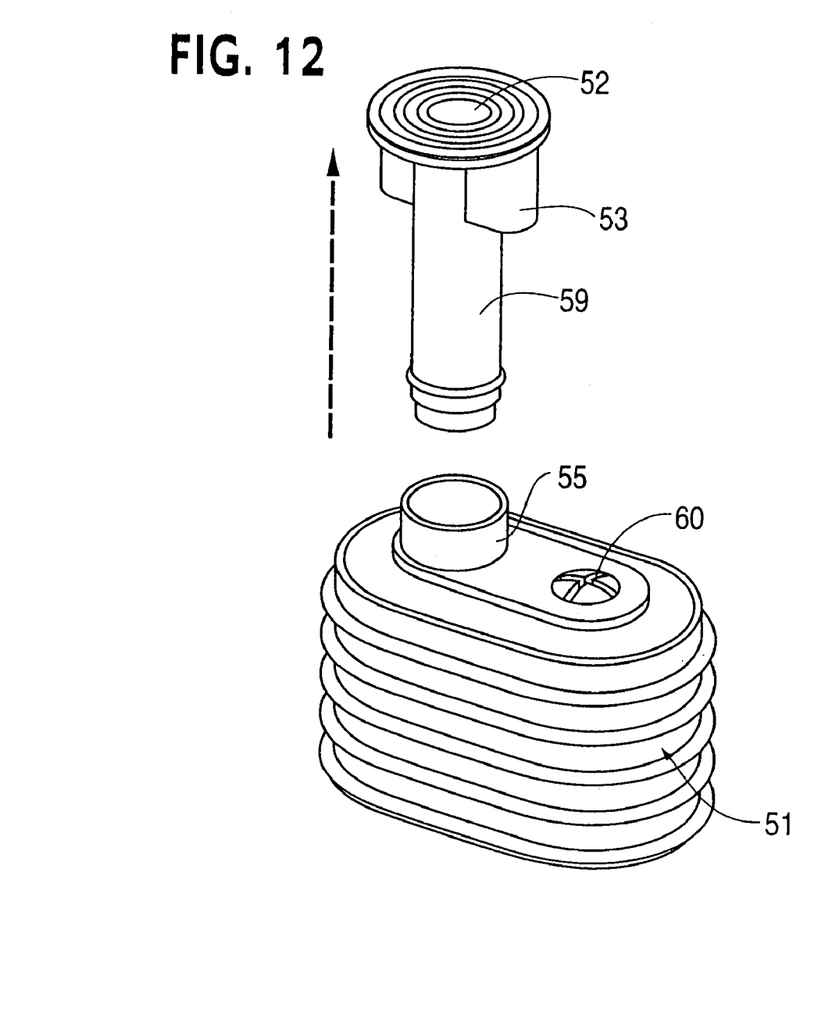
FIG. 12 is an exploded view of the apparatus of FIG. 9.
Figure 13:
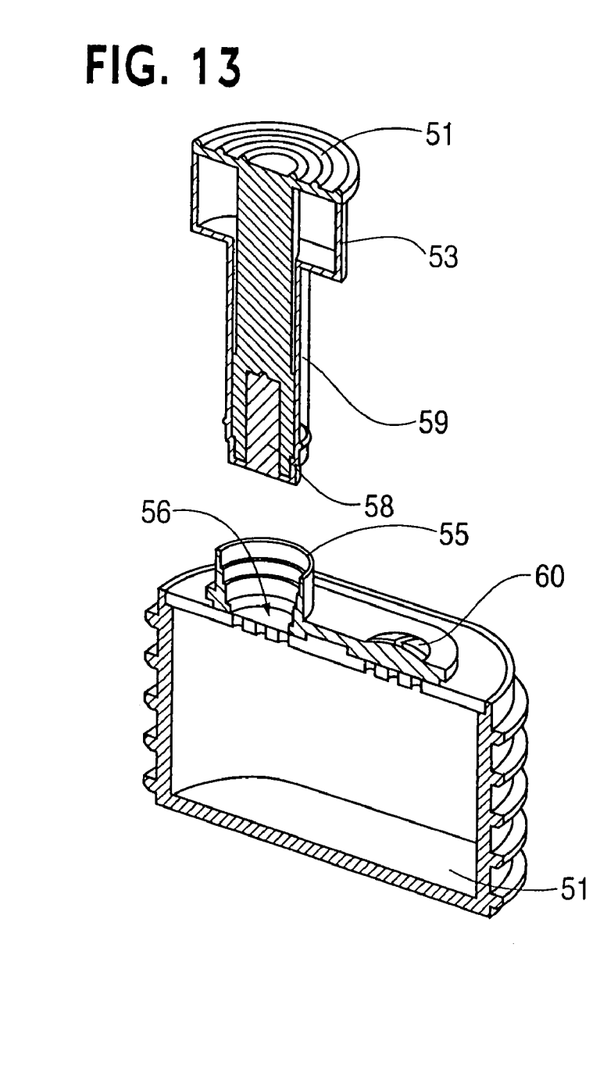
FIG. 13 is a cross-sectional view of the apparatus of FIG. 9.

A shown in FIGS. 12 and 13, the waste container 51 further includes a well 55 for attaching the tube 59 to the waste container 51.

Figure 11:
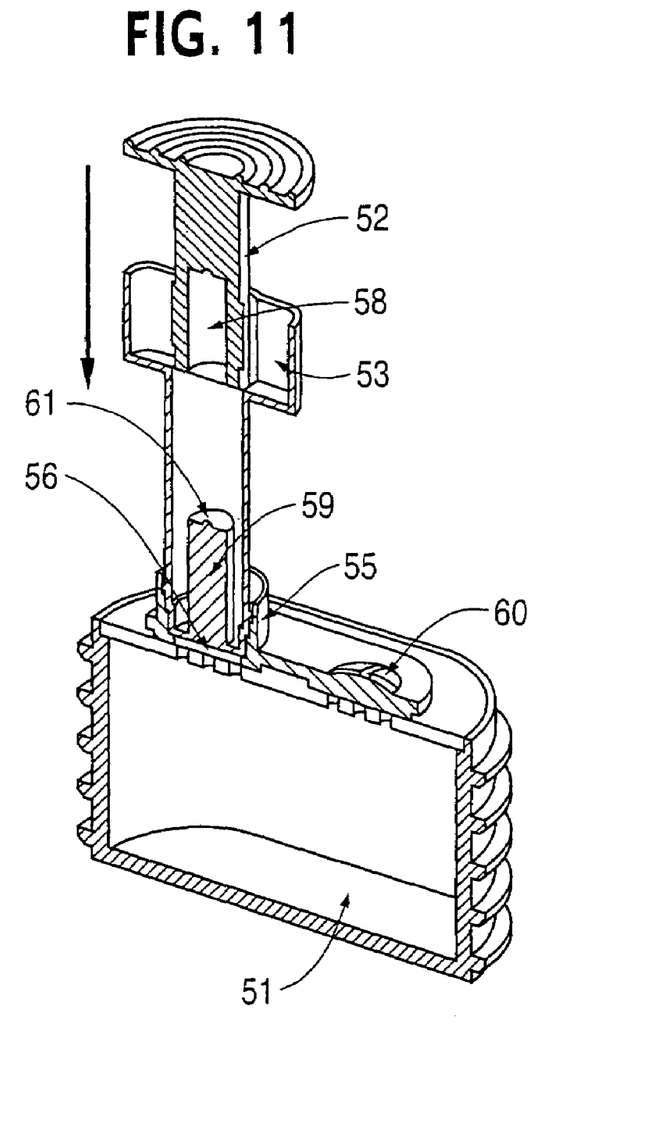
FIG. 11 is a cross-sectional view of the apparatus of FIG. 9.

As shown in FIG. 11, the plunger 52 includes a buffer compartment 58. The buffer compartment 58 is at an end of the plunger 52. A spike 61 is positioned in the tube 59 and configured to rupture the buffer compartment 58 when the plunger 52 is depressed. When the buffer compartment 58 is ruptured, a buffer is released to wash inhibitors off particles of a liquid sample. The buffer (not pictured) washes the inhibitors off and passes through a filter 56 and into the waste container 51.

The filter 56 is positioned inside the well 55 and configured to receive a buffer and the liquid sample and collect a portion of the prepared liquid sample.

The tube 59 and plunger 52 may be detached from the waste container 51 and discarded.

The waste container 51 may include a material, such as Watersorb, to absorb the waste liquid sample that passes through the filter 56.

Figure 14:
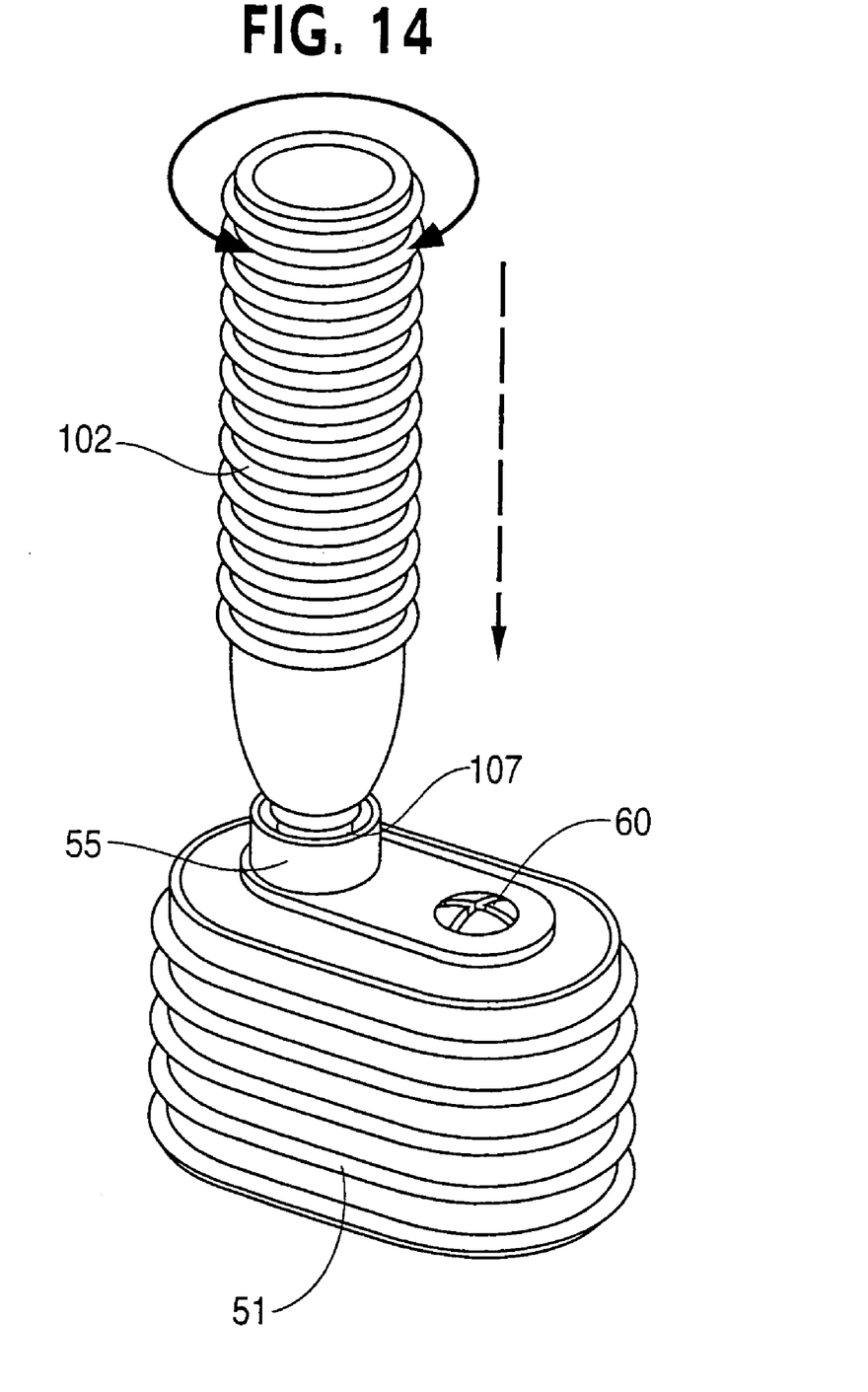
FIG. 14 is a view of the apparatus of FIG. 9.

As can be seen in FIG. 14, the well 55 of the waste container 51 is configured to receive a swab 107 of a handle 102. The swab 107 is inserted into the well 55 and collects a specimen of the prepared liquid sample.

The sample is collected on the absorbent material 103 and is prepared for analysis as described in the previous embodiment, FIGS. 1–8.

The waste container 51, as shown in FIGS. 9–14, may include a vent 60. The waste container 51 may also include a handgrip 57 configured to be handled by a gloved hand.

The apparatus 50 may be constructed of a suitable size and weight so that it may be easily transported for use in the field. For example, the apparatus 50 may be carried in the operator's hand for simple portability.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. An apparatus for preparing samples for Polymerase Chain Reaction analysis comprising:
   a handle;
   a swab, including a chamber, attached to an end of the handle, wherein the swab includes a stabilized reagent in the chamber and a sample tube extending from an end of the chamber; and
   a wand assembly including a buffer container at an end of a shaft and a stand at another end of the shaft;

wherein the handle is configured to be attached to the wand assembly, and wherein the wand assembly includes an extendable grip.

2. The apparatus of claim 1, wherein the buffer container includes a film covering one end of the container.

3. The apparatus of claim 1, further comprising a spike positioned in the wand assembly and configured to rupture the buffer container to allow a buffer to exit the buffer container and flow into the chamber.

4. The apparatus of claim 1, wherein the chamber includes vents.

5. The apparatus of claim 1, wherein the handle removably attaches to the wand assembly by the swab inserting into the shaft of the wand assembly.

6. The apparatus of claim 5, wherein a cover of the handle is configured to detach from the swab when the swab is attached to the wand assembly.

7. The apparatus of claim 1, wherein the stand is configured to attach to a slot in a hand-held detector for biological materials.

8. The apparatus of claim 1, wherein the handle and wand assembly are configured to be portable.

9. The apparatus of claim 1, further comprising an absorbent material attached at an end of the swab.

10. The apparatus of claim 9, wherein the absorbent material is held in place by a retaining ring.

11. The apparatus of claim 9, wherein a mesh covers the absorbent material.

12. The apparatus of claim 9, further comprising a mesh underneath the absorbent material.

13. The apparatus of claim 9, wherein the absorbent material comprises paper.

14. A biological sampling method for dry and/or processed samples, comprising the following steps:

providing a handle containing an absorbent material and stabilized reagent and wiping the absorbent material over a test surface; and providing a wand assembly and inserting the handle into the wand assembly, thereby rupturing a buffer container to enable a buffer to be released through the absorbent material and into a chamber for mixing with the reagent and filling a sample tube;

sealing the chamber by fully inserting a swab of the handle into the wand assembly;

extending a grip on the wand;

removing a cover on the swab, and moving the wand by executing two whip actions wherein one end of the wand is moved over an arcuate distance that is greater than another end of the wand;

retracting the grip on the wand; and inserting the wand into a hand-held detector for biological materials.

15. The method of claim 14, wherein the buffer container is ruptured by rupturing a film covering one end of the container.

16. The method of claim 14, wherein the absorbent material comprises paper.

17. The method of claim 14, wherein the absorbent material is covered by a mesh.

18. The method of claim 14, further comprising a mesh under the absorbent material.

19. An apparatus for preparing samples for Polymerase Chain Reaction analysis comprising:

a handle;

a swab, including a chamber, attached to the handle, wherein the swab includes a reagent in the chamber and a sample tube in fluid communication with the chamber; and a wand assembly including an extendable grip and a buffer container containing a buffer, the apparatus being adapted to direct the buffer from the buffer container and into the chamber;

wherein the handle is configured to be attached to the wand assembly.

20. The apparatus of claim 19, wherein the buffer container includes a film covering one end of the container.

21. The apparatus of claim 19, further comprising a spike positioned in the wand assembly and configured to rupture the buffer container to allow a buffer to exit the buffer container and flow into the chamber.

22. The apparatus of claim 19, wherein the chamber includes vents.

23. The apparatus of claim 19, wherein the handle removably attaches to the wand assembly by the swab inserting into the shaft of the wand assembly.

24. The apparatus of claim 23, wherein a cover of the handle is configured to detach from the swab when the swab is attached to the wand assembly.

25. The apparatus of claim 19, wherein the handle and wand assembly are configured to be portable.

26. The apparatus of claim 19, further comprising an absorbent material attached at an end of the swab.

27. The apparatus of claim 26, wherein the absorbent material is held in place by a retaining ring.

28. The apparatus of claim 26, wherein a mesh covers the absorbent material.

29. The apparatus of claim 26, further comprising a mesh underneath the absorbent material.

* * * * *